United States Patent [19]

Descamps et al.

[11] 4,007,204
[45] Feb. 8, 1977

[54] BENZOTHIOPHENE COMPOUNDS AND THE PRODUCTION AND USE THEREOF

[75] Inventors: Marcel Descamps, Crainhem; Jean Gubin, Brussels, both of Belgium

[73] Assignee: Labaz, Paris, France

[22] Filed: Apr. 21, 1975

[21] Appl. No.: 569,819

[30] Foreign Application Priority Data

June 6, 1974 United Kingdom ............ 25256/74

[52] U.S. Cl. .......................... 260/330.5; 424/275
[51] Int. Cl.$^2$ ...................... C07D 333/52
[58] Field of Search ..... 260/329 F, 329 AM, 330.5, 260/332.3 P; 424/275

[56] References Cited

UNITED STATES PATENTS 3,658,845  4/1972  Posselt et al. .................. 260/330.5
3,706,747  12/1972  DeAngelis et al. .......... 260/265.5 A

OTHER PUBLICATIONS

Belgium Patent 804,550 (Derwent No. 21007V) 6/3/74.

Primary Examiner—James O. Thomas, Jr.
Assistant Examiner—A. Siegel
Attorney, Agent, or Firm—Mason, Kolehmainen, Rathburn & Wyss

[57] ABSTRACT

Novel benzo[b]thiophene derivatives corresponding to the general formula:

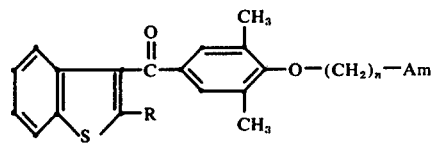

and the pharmaceutically acceptable acid addition salts thereof, wherein R represents a branched- or straight-chain alkyl group containing from 1 to 4 carbon atoms, or a cyclohexyl group, $n$ is an integer in the range of from 3 to 6 inclusive, and Am represents a dimethylamino, diethylamino, di-n-propylamino or di-n-butylamino group.

These derivatives are useful for the treatment of pathological conditions of the heart and in particular angina pectoris.

1 Claim, No Drawings

BENZOTHIOPHENE COMPOUNDS AND THE PRODUCTION AND USE THEREOF

This invention relates to heterocyclic compounds and is concerned with novel benzo[b]thiophene derivatives and pharmaceutical compositions containing the same, and with a process for preparing the said benzo[b]thiophene derivatives.

The benzo[b]thiophene derivatives with which the present invention is concerned are the compounds represented by the general formula:

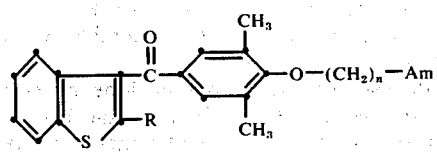

and the pharmaceutically acceptable acid addition salts thereof, for example the oxalate or hydrochloride, wherein R represents a branched- or straight-chain alkyl group containing from 1 to 4 carbon atoms, or a cyclohexyl group, $n$ is an integer in the range from 3 to 6 inclusive, and Am represents a dimethylamino, diethylamino, di-n-propylamino or di-n-butylamino group.

The compounds of formula I can be prepared, in accordance with the invention, by condensing, advantageously in an inert organic medium such as, for example, dimethylformamide, an alkali metal salt, preferably the potassium or sodium salt, of an appropriately substituted benzo[b]thiophene derivative represented by the general formula:

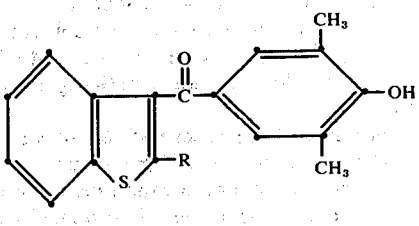

in which R has the same meaning as in formula I, with a dibromoalkane of the general formula:

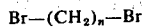

in which $n$ has the same meaning as in formula I, to form a substituted bromoalkoxy-benzoyl-benzo[b]thiophene of the general formula:

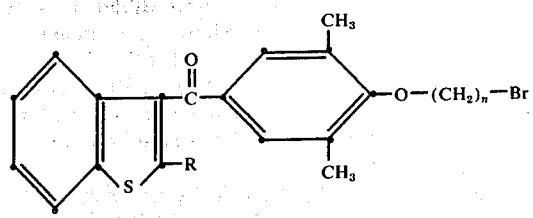

in which R and $n$ have the same meanings as in formula I, and condensing the compound of formula IV with an amine of the general formula:

in which Am has the same meaning as in formula I, the condensation advantageously being effected in an inert solvent such as, for example, benzene, to form the required benzo[b]thiophene derivative of formula I which, if desired, is reacted with an appropriate acid to provide a pharmaceutically acceptable acid addition salt thereof.

The compounds of formula I in which $n$ is 3 may alternatively be prepared by condensing, advantageously in an inert organic medium such as, for example, benzene or dichlorethane, an alkali metal salt, preferably the potassium or sodium salt, of an appropriately substituted benzo[b]thiophene derivative represented by the general formula:

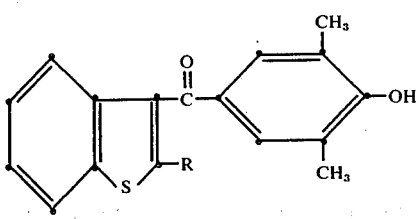

wherein R has the same meaning as in formula I, with an alkylamino derivative represented by the general formula:

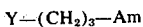

or an acid addition salt thereof, in which Y represents a halogen atom or a tosyloxy radical and Am has the same meaning as in formula I to form the required compound of formula I, which if desired, is reacted with an appropriate acid to provide a pharmaceutically acceptable acid addition salt of the benzo[b]thiophene derivative of formula I.

The compounds of formula II can be prepared by condensing, by Friedel-Crafts reaction, 2,6-dimethylanisole with a 3-carboxybenzo[b]thiophene acid chloride of the general formula:

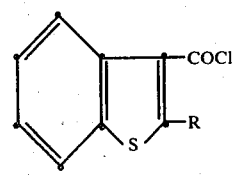

wherein R has the same meaning as in formula I to give the corresponding 3-anisoyl-benzo[b]thiophene of the general formula:

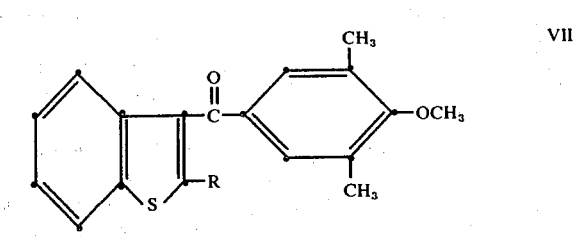

wherein R has the aforesaid meaning. The compounds of formula VII are then demethylated with pyridine hydrochloride to give the corresponding compound of formula II.

2,6-Dimethyl-anisole is already known, having been published by Baldwin and Robinson in the Journal of the Chemical Society 1264 (1934).

The compound of formula VI in which R represents methyl is a known compound, having been described by F. SAUTER, L. GOLSER and P. STUETZ, in MONATSH. CHEM. 98, 2089 (1967).

The compounds of formula VI in which R represents a branched- or straight-chain alkyl group containing from 2 to 4 carbon atoms or a cyclohexyl radical, can be prepared by known procedures by reacting an appropriately substituted benzo[b]thiophene acid derivative of the general formula:

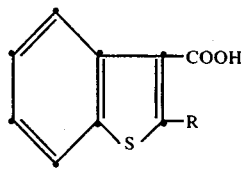

VIII wherein R has the aforesaid meaning with, for example, thionyl chloride.

The compounds of formula VIII can be obtained by the halo-form reaction described by F. SAUTER, L. GOLSER and P. STUETZ in MONATSH. CHEM. 98, 2089 (1967) applied to the appropriately substituted 3-acetylbenzo[b]thiophene derivatives of the formula:

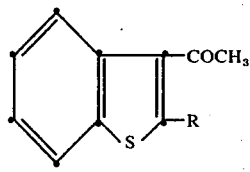

IX wherein R has the same meaning as in formula VIII.

The compounds of formula IX are either known compounds having been described by R. ROYER, P. DEMERSEMAN and A. CHEUTIN in Bull. Soc. Chim. Fr. 1534 (1961) and by P. FALLER in Bull. Soc. Chim. Fr. 934 (1969), or may be prepared by the method described in these publications.

The compounds of the invention have been found to possess useful pharmacological properties capable of rendering them of considerable value in the treatment of pathological conditions of the heart. In particular, the compounds of the invention have been found to possess properties capable of rendering them extremely useful in the treatment of angina pectoris.

Another object of the invention is therefore a method of treating pathological conditions of the heart and in particular angina pectoris in a subject in need of such treatment by administering to the said subject at least one compound of formula I or a pharmaceutically acceptable acid addition salt thereof.

It is a well-known fact that pathological conditions of the heart are very difficult diseases to master.

This is particularly true in the case of angina pectoris. This disease most certainly involves, in addition to physiological cardiac deficiencies, profound and long-standing mental factors. This explains, in part at least, why this disease is mainly prevalent amongst people who are overconscientious by nature or whose professional life is devoted to the handling of problems which involve considerable responsability and impose severe mental and moral stress.

Treatment of the disease is further complicated by the fact that not all patients respond to the same therapy while in some cases a particular therapy, probably for reasons peculiar to the patient, ceases to be effective and must be replaced by another.

However, much can be done to alleviate this condition not only by treatment of the disease at the very site of its occurrence but also by modifying certain physiological factors which, taken together, contribute to the development of this particular pathological condition.

An appreciable amount of work has been done in this field and the responsible research workers can look with some pride on the not inconsiderable results obtained so far.

Nevertheless, much remains to be done and no doubt at some time in the future this particular form of cardiac dysfunction will be brought under a reasonable degree of control.

The inventors of the present series of compounds do not claim that they have found the final answer to this highly prevalent and very varied pathological cardiac condition. They do, however, contend that they have made a step forward towards this ultimate goal in producing compounds which, surprisingly enough, offer certain advantages over the anti-anginal agents so far employed in current medical practice.

A very comprehensive article published by R. CHARLIER in the Nouvelle Presse Medicale, 1974, 3, pp 2407–2410 provides an excellent survey of the anti-anginal agents so far used, enumerating their respective advantages and drawbacks.

The author of this article, who has worked for many years on the problems of the treatment and the mechanism of angina pectoris and has produced numerous publications including two books on the subject, provides a list of the conditions which, in the light of present medical knowledge, the ideal anti-anginal agent should fulfill.

These conditions may be described as follows:
1. Because during an attack of angina pectoris the patient's myocardium consumes too much oxygen, it is desirable to reduce the oxygen requirements of the myocardium. This involves a reduction of cardiac frequency and, as far as is possible, a lowering of arterial blood pressure.
2. For the same reason, it is desirable to increase the supply of oxygen to the myocardium or, in other words, to step up the flow of blood to the heart-muscle.
3. Since attacks of angina pectoris are provoked by stimulation of the sympathetic nervous system which leads to the release into the bloodstream of catecholamines such as adrenaline and nor-adrenaline, it is important that an anti-anginal agent should possess anti-adrenergic properties and thus combat, at least partially, the tachycardia and increased arterial blood pressure which result from stimulation of the sympathetic nervous system.
4. The performance of the cardiac muscle should not be further depressed with respect to its haemodynamic role i.e. cardiac output. It should, in fact, be stimulated to a certain degree.

The author first deals with the nitrites which improve the supply of oxygen to the myocardium without depressing cardiac functioning but do not reduce cardiac frequency. This is followed by a discussion of the series of compounds comprising prenylamine, benziodarone, imolamine, iproveratril, hexobendine, oxyfedrine, fenalcomine, dipyridamole, carbochromene and lidoflazine which have undoubted value as coronary vasodilators devoid of any depressant effect upon cardiac functioning but which do not reduce the oxygen requirements of the myocardium or inhibit the cardiovascular reactions to adrenergic stimulants. Attention is then given to the β-blocking agents such as propranolol, practolol, oxprenolol, alprenolol, pindolol and sotalol. These agents are of undoubted value in the treatment of angor as they diminish the oxygen requirements of the myocardium by considerably reducing cardiac frequency. They also exert an anti-adrenergic effect. However, they lower the supply of oxygen to the myrocardium and depress cardiac functioning. Another more recent agent discussed is perhexiline maleate which combines the qualities of increasing the supply of oxygen to the myocardium while at the same time diminishing cardiac frequency and thereby reducing the oxygen requirements of the myocardium. Furthermore, perhexiline maleate does not appear to exert a depressant effect upon cardiac functioning. However, this substance does not possess any anti-adrenergic properties and although it may be classed amongst the most promising anti-anginal agents, its proper position in the anti-anginal therapeutic arsenal remains to be determined by exhaustive clinical trials.

Finally, the article in question deals with amiodarone which for some years now has been clinically used as a very successful anti-anginal agent. According to the author, this substance possesses the four qualities which are at present recognized as being required to provide a useful, effective and outstanding anti-anginal drug.

Amongst these various agents which, taken together, constitute an excellent summary of the prior art, Applicants feel that the most suitable for comparison purposes is that known as amiodarone.

In the first instance, this substance is an outstanding example of the type of drug currently used to alleviate anginal conditions and in the second instance it presents all the qualities which, according to present medical knowledge and thinking, are required to combat effectively an anginal condition.

Finally, what is perhaps more important still, amiodarone presents, chemically speaking, a considerable degree of similarity to the series of products forming one of the objects of the present invention.

In consideration of these factors, comparative trials were carried out with the preferred compound of the present invention, namely:

2-methyl-3-(3,5-dimethyl-4-γ-di-n-butylamino-propoxy-benzoyl)-benzo[b]thiophene, hereinafter referred to as The Compound, in the form of a pharmaceutically acceptable acid addition salt with amiodarone of which the formula is:

2-n-butyl-3-(3,5-diiodo-4-β-N-diethylaminoethoxy-benzoyl)-benzofuran, hereinafter referred to as amiodarone, also in the form of a pharmaceutically acceptable acid addition salt.

In carrying out these tests, both The Compound and amiodarone were administered intravenously in a dose of 10 mg/kg. In both cases a 5% aqueous solution of the hydrochloride salt was used and the injection of 10 mg/kg took 2 minutes to administer.

1. The first test aimed at determining the respective capabilities of the two substances to reduce the oxygen requirements of the myocardium.

This property was measured by the indirect method known as the tension-time index which is a widely used and accurate haemodynamic index of myocardial oxygen needs. This method requires three cardiovascular parameters to be measured simultaneously, namely the mean aortic systolic blood pressure, the heart rate and the duration of the left ventricular blood ejection. The figure representing the tension-time index per minute is obtained by multiplying the means aortic systolic blood pressure expressed in mm Hg by the duration in seconds of the left ventricular blood ejection and multiplying the result by the number of heart beats per minute. This provides an index of the total amount of oxygen used by the myocardium over a period of one minute. As it thus represents an accurate indication of the oxygen consumption of the myocardium, any lowering of the tension-time index indicates a corresponding drop in the oxygen consumption of the myocardium. The value of this system of measurement is clearly described for example by S.J. SARNOFF et al. in the Amer. J. Physiol., 192, 148 (1958).

The test was carried out on mongrel dogs of both sexes weighing between 14 and 26 kg which had been previously anaesthetized with pentobarbital (30 mg/kg by intravenous route) and intubated with a Rusch tracheal cannula. The method used to measure the requisite parameters was that described by R. CHARLIER and J. BAUTHIER in Arzneimittel-Forschung "Drug Research" 23, n 19, 1305–1311 (1973) and involved the use for both The Compound and amiodarone of some 10 to 15 dogs.

The pharmacological trials thus performed showed that The Compound exerts approximately the same effect as a reducer of the oxygen consumption of the myocardium as does amiodarone. In this respect, the two compounds may be considered as being of equal value.

In one particular instance, in order to obtain a rapid check on the relative values of The Compound and amiodarone in this respect, trials were carried out on two dogs chosen at random. The results obtained in this particular trial showed that The Compound exerted a markedly superior effect as a reducer of the oxygen consumption of the myocardium than that obtained with amiodarone, the comparative results being as follows:

| Intervals of Measurement | Oxygen Consumption | |
|---|---|---|
| | The Compound | Amiodarone |
| | (Dog n° 6009) | (Dog n° 6013) |
| Before administration of the product | 100% | 100% |
| 2.5 min. after administration | 63.3% | 76.5% |
| 5 min. after administration | 68.9% | 80.7% |
| 10 min. after administration | 74.3% | 80.3% |
| 20 min. after administration | 74.0% | 78.6% |
| 30 min. after administration | 77.2% | 74.9% |
| 60 min. after administration | 77.1% | 78.9% |

These Figures are cited merely to demonstrate the decided superiority shown by The Compound in this particular instance. However, Applicants readily admit that pharmacological trials are never mathematically constant and that the overall results obtained in tests involving a large number of animals tend to reduce to very small limits the activity difference between compounds. This is, of course, explained by the sometimes considerable difference in response between one animal and another. For this reason, Applicants conclude that, with respect to the reduction of the oxygen consumption of the myocardium, The Compound and amiodarone may reasonably be considered to be of approximately equal value, the average results showing a reduction of between 15% and 20% after 60 minutes.

2. A second series of tests were carried out in order to determine the capability of The Compound and of amiodarone of increasing the blood flow to the myocardium and thus stepping up the supply of oxygen to this muscle. These tests were carried out in accordance with the technique described by R. CHARLIER and J. BAUTHIER in the above-cited Arzneimittel-Forschung "Drug Research" reference. The tests involved some 10 to 20 dogs each of which received the substance being tested in a dose of 10 mg/kg by intravenous route. Here again, it was found that the effect of The Compound was approximately equal to that of amiodarone, the increase in blood-flow to the myocardium being between 80% and 100% and returning to its initial value after 20 to 30 minutes. The results were in fact slightly in favour of amiodarone but in view of the necessarily varied nature of results obtained in animal trials of this kind, Applicants can reasonably conclude that the two substances are equal with regard to their capability of increasing the blood flow to the myocardium.

3. In the third series of tests performed in order to compare the respective capabilities of The Compound and amiodarone to reduce, in atropinized dogs (1 mg/kg by intravenous route), the increase in tension-time index i.e. to reduce the increase in the oxygen requirements of the myocardium provoked by either 3 $\mu$g/kg of adrenaline or 2 $\mu$g/kg of nor-adrenaline, it was found that The Compound was markedly superior to amiodarone.

The method of determination of the results was the same as that described by R. CHARLIER and J. BAUTHIER in the above Arzneimittel-Forschung "Drug Research" reference.

In the case of adrenaline the tension-time index was considerably increased in 5 dogs by the above-cited dose of 3 $\mu$g/kg which was given at 0 minute less 20 and again at 0 minute less 10 minutes. The average value of the tension-time index increases obtained with the above dose of adrenaline at 0 minute less 20 minutes and at 0 minute less 10 minutes was calculated as 75%. At 0 minute, when the tension-time index had returned to its initial level to which the value 100% was attributed, a dose of 10 mg/kg of The Compound was given intravenously. Ten minutes later the same dose of adrenaline was administered and the tension-time index only showed an increase of 14% while further doses of the same quantity of adrenaline administered at periods of 20, 30 and 60 minutes after the single injection of The Compound which had been given at 0 minute showed respective tension-time index increases of 35%, 31% and 33%.

The same test performed under the same conditions on five dogs with amiodarone showed that from an average tension-time index increase of 75%, the tension-time index increases at 10, 20, 30 and 60 minutes after the injection of 10 mg/kg of amiodarone were respectively 39%, 38%, 44% and 73%.

From this it is clear that the anti-adrenergic action of The Compound against the undesirable effects of adrenaline is vastly superior to that of amiodarone and furthermore is of considerably longer duration.

A similar result was obtained with six atropinized dogs which were given 2 $\mu$g/kg of nor-adrenaline intravenously 20 minutes and again 10 minutes before 0 minute.

In the test involving The Compound, these two doses of nor-adrenaline gave an average tension-time index increase of 43%. At 0 minute, when the tension-time index had returned to its initial level to which the value 100% was attributed, a dose of 10 mg/kg of The Compound was administered intravenously and 10, 20, 30 and 60 minutes after this single dose of The Compound, further doses of 2 $\mu$g/kg of nor-adrenaline were given intravenously. These four doses of the catecholamine resulted in respective tension-time index increases of 10%, 19%, 21% and 22%.

Under the same conditions, the test involving amiodarone showed that, from an average tension-time index increase of 40%, the tension-time index increases at 10, 20, 30 and 60 minutes after the injection of 10 mg/kg of amiodarone were respectively 22%, 25%, 30% and 42%. Thus, while The Compound produced and maintained an appreciable drop in the tension-time index increase over a period of 60 minutes, amiodarone, under the same circumstances, produced a smaller drop in the tension-time index increase and furthermore allowed the tension-time index value to return after 60 minutes to a little above the average increase of 40% registered on the basis of the injections of nor-adrenaline given at 20 minutes and 10 minutes before 0 minute.

This shows that, in the case of nor-adrenaline, The Compound, as a reducer of the nor-adrenaline-induced increase in tension-time index, is not only considerably more powerful than amiodarone but its action lasts appreciably longer.

4. In the fourth test relating to cardiac output, comparative trials were carried out in oder to determine the relative values of The Compound and amiodarone in this respect.

The dose of each substance was 10 mg/kg by intravenous route and the method employed was that described in Arzneimittel-Forschung (Recherches sur les Medicaments) 22, 1698–1703 (1972) by R. CHARLIER, G. DELAUNOIS and J. BAUTHIER. In each series of trials, 10 mongrel dogs were used.

Here it should be emphasized that cardiac output in the evaluation of an anti-anginal drug is particularly valuable because it involves different factors which themselves play an important part in alleviating angina pectoris.

The different factors involved are stroke volume i.e. the amount of blood ejected at each systolic beat by the left ventricle and the number of heart-beats per minute. As stated above, it is desirable to reduce the number of heart-beats per minute and at the same time increase cardiac output. This means that the result aimed at is to step up stroke volume.

At the present time there does not exist any established means of measuring stroke volume, but cardiac output on the other hand can be measured with accuracy. Thus, in order to determine the effect of any particular substance on stroke volume, it is sufficient to divide cardiac output by the number of heart-beats per minute. Thus, if the initial cardiac output of an animal were 2000 ml and cardiac frequency 100, the corresponding stroke volume would be 20 ml. If the cardiac output is brought up to 3000 ml i.e. a 50% increase and cardiac frequency is lowered to 80 i.e. a drop of 20% the stroke volume becomes 3000 divided by 80 which gives a stroke volume of 37.5. This represents an increase of 17.5 over the initial 20 ml of stroke volume or approximately 90%.

In the comparative trials carried out with The Compound and amiodarone with respect to cardiac output it was found in the case of The Compound that the increases after 2.5 minutes and 5 minutes were respectively 150% and 141% as against 121.5% and 123% for amiodarone after the same periods of time.

Here it should be mentioned that, as pointed out in Arzneimittel-Forschung "Drug Research" — January 1975, page 47, the variations measured at periods beyond 5 minutes are not statistically significant when compared to the results obtained with the control animals which only received a volume of saline equivalent to that of the substance under study.

In measuring cardiac frequency each dog was given an initial value of 100% at 0 minute i.e. the moment when the compound under study was administered.

In the case of The Compound, it was found that after 2.5 minutes and 5 minutes cardiac frequency had dropped respectively to 80% and 74% while the corresponding Figures for amiodarone were 92% and 87%.

These Figures give increases in stroke volume of 90% and 93% for The Compound after 2.5 minutes and 5 minutes as against 32.5% and 43.5% for amiodarone after the same periods of time.

These findings show that The Compound proved to be considerably superior to amiodarone with regard to the phase of increase in stroke volume and cardiac output which represents a stimulation of this extremely important aspect of cardiac functioning.

In the four trials thus carried out The Compound was found to be equal to amiodarone in the first two and superior to amiodarone in the last two. From this it may be concluded that the overall value of The Compound is greater than that of amiodarone. Applicants are aware that although amiodarone by its therapeutic efficacy and chemical similarity to the compounds of the invention represents an excellent illustration of the state of the art, it may be useful to compare The Compound with the preferred compound of British Patent No. 1,382,742, which, being dimethylated on the benzoyl ring, is also very close, chemically speaking, to The Compound.

The said preferred compound of British Patent No. 1,382,742 is: 2-ethyl-3-(3,5-dimethyl-4-γ-di-n-butylaminopropoxy-benzoyl)-benzofuran (hereinafter referred to as L 8412).

Here also the four tests described above were carried out with L 8412 and the following results were registered.

1. In all, 15 mongrel dogs were used, each of which received 10 mg/kg of L 8412 by intravenous route.

The results obtained showed that the activity of L 8412 and of The Compound as reducers of the oxygen consumption of the myocardium is the same, both substances being equal in this respect to amiodarone.

2. In the second test which was carried out on 12 dogs to determine the capability of L 8412 of increasing the blood flow to the myocardium, it was found that an intravenous injection of 10 mg/kg of this substance produced a peak increase of 55% after 3 minutes and returned to the initial value at the end of 10 minutes.

In this test, The Compound proved to be markedly superior to L 8412 as the peak increase produced by The Compound was 80% after 3 minutes and the blood flow to the myocardium did not return to its initial value until 20 minutes had elapsed.

3. The third test which was carried out with a view to determining the capability of L 8412 of reducing in dogs the increase in tension-time index experimentally provoked by adrenaline or nor-adrenaline was divided into two parts as above.

The first part involved 5 dogs each of which received 30 minutes and 15 minutes before 0 minute an intravenous dose of 3 μg/kg of adrenaline which gave an average increase in tension-time index of 72%. At 0 minute, when the tension-time index had returned to its initial level to which the value 100% was attributed, a dose of 10 mg/kg of L 8412 was given intravenously. The same dose of adrenaline was administered at periods of 10, 20, 30 and 60 minutes after 0 minute. The results registered showed respective increases in tension-time index of 6%, 14%, 16% and 28% at the four periods indicated. In this particular part of this test, the effect of L 8412 was superior to that of The Compound which, from an average tension-time index increase of 75%, showed tension-time index increases of 14%, 35%, 31% and 33% at the four periods indicated.

In the second part, 4 dogs were used each of which received 30 minutes and 15 minutes before 0 minute an intravenous dose of 2 μg/kg of nor-adrenaline which gave an average increase in tension-time index of 66%. At 0 minute, when the tension-time index had returned to its initial level to which the value 100% was attributed, a dose of 10 mg/kg of L 8412 was given intravenously. The same dose of nor-adrenaline was administered at periods of 10, 20, 30 and 60 minutes after 0 minute. The results registered showed respective increases in tension-time index of 11%, 21%, 22% and 25% at the four periods indicated. In this part of the test L 8412 proved to be slightly superior to The Compound which, from an average tension-time index increase of 43%, showed tension-time index increases of 10%, 19%, 21% and 22% at the four periods indicated.

4. In the fourth test which aimed at determining cardiac output the same experimental conditions were observed as above and after 2.5 minutes and 5 minutes cardiac output with L 8412 was found to be respectively 115% and 105% as opposed to 150% and 141% with The Compound.

As in the previous cardiac output test, each dog was given an initial value of 100% at 0 minute with regard to cardiac frequency.

In the case of The Compound, the result was, as already indicated, that cardiac frequency dropped to 80% and 74% after 2.5 minutes and 5 minutes. The corresponding figures for L 8412 were 82% and 74.5%.

These figures give stroke volume increases of 90% and 93% for The Compound as against 40% and 41% for L 8412.

This shows that The Compound proved to be markedly superior to L 8412 with regard to the phase of increase in stroke volume and cardiac output which represents a stimulation of this extremely important aspect of cardiac functioning.

Thus out of four tests, it was found that The Compound proved to be equal to L 8412 in the first test, inferior in the third test and markedly superior in the very important second and fourth tests.

In the light of these findings, Applicants conclude that The Compound represents an appreciable step-forward with respect to L 8412.

Other comparative pharmacological tests were carried out with compounds of the invention. Although these pharmacological tests are less elaborate than those described above, they nevertheless constitute a reliable guide with regard to the selection of compounds which are likely to be useful as a means of treating pathological heart conditions and in particular angina pectoris.

In this connection, it should be emphasized that, as stated above, pathological heart conditions and particularly angina pectoris are very difficult to treat. It is certain that no one single drug is ever likely to be developed which will be effective in all instances. Thus, it is imperative that the physician should have at his disposal a selection of drugs from which he can choose that which is most suitable for a particular case. It does, in fact, very often happen that, for various reasons, the physician finds it advantageous to switch from one drug to another in order more effectively to combat a particular phase of the disease. One of the reasons for this may be the mental attitude which a patient develops towards a particular drug. Other reasons may be simple habituation to one formula or a change in the patient's pathological heart condition which necessitates the adoption of another and equally active compound. It is the purpose of the inventors of the present series of compounds to provide just such replacement medication and thus furnish the physician with the variety of weapons which he requires to bring relief to or to prolong relief in a heart patient.

The comparative pharmacological trials carried out for the abovementioned selection purposes may be described as follows. They number four in all and bear the references A, B, C and D.

Trial A

A dose of the compound was administered intravenously to a normal dog for the purpose of reducing cardiac frequency. The reduction in cardiac frequency was noted in terms of a percentage of the initial heart-rate.

Trial B

The purpose of this trial was to determine the reduction in arterial blood-pressure obtained by the intravenous administration to a normal dog of a dose of the compound under study. The reduction in arterial blood-pressure was recorded as a percentage of the initial pressure.

Trial C

The purpose of this trial was to determine the percentage by which a dose of the compound under study reduced the isoprenaline-accelerated heart-rate in a dog which had previously received an intravenous dose of 1 mg/kg of atropine sulphate. The difference between the maximum accelerated heart-rate and the initial heart-rate was noted and expressed as a percentage of the latter. This percentage for purposes of convenience is referred to as X. After the effects of the isoprenaline had disappeared, a dose of the compound to be tested was administered intravenously. The animal then received the same quantity of isoprenaline as before and it was observed that the degree of maximum acceleration in cardiac frequency was less than that previously recorded. This new difference was noted and converted to a percentage of the heart-rate figure recorded before the second administration of isoprenaline. This latter percentage is referred to herein as Y. Finally, Y was subtracted from X and the result was registered as a percentage of X.

Trial D

The purpose of this trial was to determine the capacity of compounds of the invention to reduce adrenaline-increased blood-pressure in the dog which had also previously received an intravenous dose of 1 mg/kg of atropine sulphate. The same procedure was followed as in Trial C with regard to the calculation of the percentage of pressure-reduction obtained.

For the purposes of expressing the results of these trials, the two compounds cited above as reference compounds namely amiodarone and L 8412 have been given the respective Nos. 1 and 2 while the formula known as The Compound bears the No. 3. In addition, the following two compounds of the invention were tested:

2-n-Propyl-3-(3,5-dimethyl-4-γ-di-n-butylamino-propoxy-benzoyl)-benzo[b]thiophene (No. 4).

2-Ethyl-3-(3,5-dimethyl-4-γ-di-n-butylaminopropoxy-benzoyl)-benzo[b]thiophene (No. 5).

All these substances were used in the form of their hydrochloride salt. Trials with each substance involved at least 12 dogs and the following results were noted:

| Compound No. | Dose Used | A | B | C | D |
|---|---|---|---|---|---|
| 1 | 10 mg/kg | 40% | 20% | 50% | 50% |
| 2 | 10 mg/kg | 40% | 20% | 50% | 50% |
| 3 | 5 mg/kg | 40% | 20% | 50% | 50% |
| 4 | 10 mg/kg | 40% | 20% | 50% | 50% |
| 5 | 10 mg/kg | 40% | 20% | 50% | 50% |

The above results show that in the four trials carried out the compounds of the invention exerted the same effect as the reference compounds with the exception of The Compound which produced the same results with only 5 mg/kg.

In connection with these trials, it should be pointed out that the reduction Figures obtained are optimal. It is quite clear that there is a limit below which it is undesirable to go when it is a question of reducing arterial blood-pressure and cardiac frequency. Such reductions are essential, according to modern medical thinking, when it is a question of diminishing the work of the heart in order to alleviate cardiac deficiencies but, as stated above, they cannot go below a certain limit without provoking undesirable side-effects. Thus, it may be said that, for the purposes for which they are required, compounds of the invention have shown in these trails that they possess the required qualities to the most recommendable degree.

It should also be noted that unlike amiodarone, the compounds of the invention are devoid of iodine which constitutes an appreciable advantage with respect to the thyroid functions of the patient.

For therapeutic use, it is recommended that the compounds of the invention be made up in single dosage units containing from 50 mg to 300 mg of active substance while the total daily dose may vary between 100 mg and 800 mg according to whether it is a question of maintenance treatment or initial treatment.

It will be appreciated that for therapeutic use the compounds of the invention will normally be administered in the form of a pharmaceutical composition which may be in a dosage unit form appropriate to the desired mode of administration. Thus, the pharmaceutical compositon may take the form of, for example, a coated or uncoated tablet, or a hard- or soft-gelatin capsule for oral administration or a suppository for rectal administration.

Irrespective of the form which the composition takes, the pharmaceutical composition will normally comprise at least one of the compounds of formula I or a pharmaceutically acceptable acid addition salt thereof associated with an appropriate pharmaceutical excipient comprising, for example, one or more of the following substances: milk, sugar, starches, talc, magnesium stearate, polyvinylpyrrolidone, alginic acid colloidal silica or flavouring agent.

The following Examples illustrate the invention.

2-ethyl-3-(3,5-dimethyl-4-γ-bromopropoxy-benzoyl)-benzo[b]thiophene - oily, not recrystallized.

b. Preparation of 2-isopropyl-3-(3,5-dimethyl-4-γ-di-n-propylaminopropoxy-benzoyl)-benzo[b]thiophene oxalate Into a 250 ml flask equipped with a condenser and a dropping-funnel, a solution of 8.9 g (0.02 mol) of 2-isopropyl-3-(3,5-dimethyl-4-γ-bromopropoxy-benzoyl)-benzo[b]thiophene in 80 ml of benzene was introduced and 14 ml (0.1 mol) of di-n-propylamine added. The reaction medium was refluxed for 20 hours and then washed with water. The organic phase was dried and carefully evaporated under vacuum so as to eliminate the excess of di-n-propylamine. The oily residue obtained was dissolved in anhydrous ether and an ethereal solution of oxalic acid was added to give a precipitate of 2.4 g of 2-isopropyl-3-(3,5-dimethyl-4-γ-di-n-propylaminopropoxy-benzoyl)-benzo[b]thiophene oxalate. Yield 22.5%; M.P. 86°C (after recrystallization from ethyl acetate).

Following the procedure described above and using the appropriate starting products, the compounds listed hereunder were prepared:

| Compound | Melting Point |
|---|---|
| 2-isopropyl-3-(3,5-dimethyl-4-γ-dimethyl-aminopropoxy-benzoyl)-benzo[b]thiophene oxalate | 173° C (after recrystallization from ethyl acetate) |
| 2-isopropyl-3-(3,5-dimethyl-4-γ-diethyl-aminopropoxy-benzoyl)-benzo[b]thiophene oxalate | 132° C (ethyl acetate) |
| 2-methyl-3-(3,5-dimethyl-4-γ-di-n-butyl-aminopropoxy-benzoyl)-benzo[b]thiophene oxalate | 128° C (ethyl acetate) |
| 2-ethyl-3-(3,5-dimethyl-4-γ-di-n-butyl-aminopropoxy-benzoyl)-benzo[b]thiophene oxalate | 127° C (ethyl acetate) |
| 2-n-propyl-3-(3,5-dimethyl-4-γ-di-n-butyl-aminopropoxy-benzoyl)-benzo[b]thiophene oxalate | 119° C (ethyl acetate) |
| 2-isopropyl-3-(3,5-dimethyl-4-γ-di-n-butyl-aminopropoxy-benzoyl)-benzo[b]thiophene oxalate | 130° C (ethyl acetate) |

EXAMPLE 1

2-Isopropyl-3-(3,5-dimethyl-4-γ-di-n-propylaminopropoxy-benzoyl)-benzo[b]thiophene oxalate.

a) Preparation of 2-isopropyl-3-(3,5-dimethyl-4-γ-bromopropoxy-benzoyl) -benzo[b]thiophene Into a one-half litre flask equipped with a mechanical stirrer and a dropping-funnel 32.5 g (0.1 mol) of 2-isopropyl-3-(3,5-dimethyl-4-hydroxybenzoyl)-benzo[b]thiophene and 28 g (0.2 mol) of anhydrous potassium carbonate were introduced with 200 ml of dimethylformamide. While stirring, 53 ml (0.5 mol) of 1,3-dibromo-propane were added and stirring was continued for 20 hours at room temperature. The mixture was then treated with a mixture of water and ether. The aqueous and organic phases were separated by decantation, the ethereal phase was dried over anhydrous sodium sulphate and then carefully evaporated in order to eliminate the excess of 1,3-dibromo-propane.

The oily residue obtained was purified by dry column chromatography using silica as absorbent to give 42.7 g of 2-isopropyl-3-(3,5-dimethyl-4-γ-bromopropoxy-benzoyl)-benzo[b]thiophene. Yield 96%.

By the procedure described above and using the appropriate starting product, the following compound was prepared:

EXAMPLE 2

2-Ethyl-3-(3,5-dimethyl-4-ω-di-n-butylaminobutoxy-benzoyl)-benzo[b]thiophene oxalate.

a. Preparation of 2-ethyl-3-(3,5-dimethyl-4-ω-bromobutoxy-benzoyl)-benzo[b]thiophene Into a 250 ml flask equipped with a mechanical stirrer and a dropping-funnel were introduced 15.5 g (0.05 mol) of 2-ethyl-3-(3,5-dimethyl-4-hydroxy-benzoyl)-benzo[b]thiophene and 14 g (0.1 mol) of anhydrous potassium carbonate with 150 ml of dimethylformamide. While stirring, 30 ml (0.25 mol) of 1,4-dibromo-butane were added and stirring was continued for 20 hours at room temperature. A mixture of water and ether was then added, the organic phase was dried over anhydrous sodium sulphate and carefully evaporated so as to eliminate the excess of 1,4-dibromo-butane. The oily residue obtained was purified by dry column chromatography using silica as absorbent.

b. Preparation of 2-ethyl-3-(3,5-dimethyl-4-ω-di-n-butylaminobutoxy-benzoyl)-benzo[b]thiophene oxalate Into a 250 ml flask equipped with a condenser and a dropping-funnel was introduced a solution of 4.45 g (0.01 mol) of 2-ethyl-3-(3,5-dimethyl-4-ω- bromobutoxy-benzoyl)-benzo[b]thiophene in 60 ml of benzene. To this solution were added 6.4 g (0.05 mol) of di-n-butylamine and the resulting mixture was refluxed for 20 hours.

The reaction medium was then washed with water and the organic phase was dried and evaporated to dryness. The oily residue obtained was dissolved in anhydrous ether and an ethereal solution of oxalic acid was added to give a precipitate of 2.3 g of 2-ethyl-3-(3,5-dimethyl-4-ω-di-n-butylaminobutoxy-benzoyl)-benzo[b]thiophene oxalate. Yield 40%; M.P. 75° C after recrystallization from benzene.

By the procedure described above and using the appropriate starting products, the compounds listed hereunder were prepared:

| Compound | Melting Point |
| --- | --- |
| 2-ethyl-3-(3,5-dimethyl-4-ω-diethylamino-butoxy-benzoyl)-benzo[b]thiophene oxalate | 142° C (methanol/acetone) |
| 2-ethyl-3-(3,5-dimethyl-4-ω-di-n-propyl-aminobutoxy-benzoyl)-benzo[b]thiophene oxalate | 66° C (benzene) |

EXAMPLE 3

2-Ethyl-3-(3,5-dimethyl-4-ω-di-n-butylaminopentoxy-benzoyl)-benzo[b]thiophene oxalate.

a. Preparation of 2-ethyl-3-(3,5-dimethyl-4-ω-bromopentoxy-benzoyl)-benzo[b]thiophene Into a 250 ml flask equipped with a mechanical stirrer and a dropping-funnel were introduced 9.3 g (0.03 mol) of 2-ethyl-3-(3,5-dimethyl-4-hydroxy-benzoyl)-benzo[b]thiophene and 10 g (0.06 mol) of anhydrous potassium carbonate with 100 ml of dimethylformamide.

While stirring 23 ml (0.15 mol) of 1,5-dibromo-pentane were added and stirring was continued for 20 hours at room temperature.

A mixture of water and ether was then added, the organic phase was dried over anhydrous sodium sulphate and carefully evaporated so as to eliminate the excess of 1,5-dibromo-pentane.

The oily residue obtained was purified by dry column chromatography using silica as absorbent.

b. Preparation of 2-ethyl-3-(3,5-dimethyl-4-ω-di-n-butylaminopentoxy-benzoyl)-benzo[b]thiophene oxalate Into a 100 ml flask equipped with a condenser and a dropping-funnel was introduced a solution of 3.4 g (0.0074 mol) of 2-ethyl-3-(3,5-dimethyl-4-ω-bromopentoxy-benzoyl)-benzo[b]thiophene in 40 ml of benzene. To this solution were added 6.5 ml of di-n-butylamine and the mixture was refluxed for 24 hours.

The reaction medium was then washed with water and the organic phase obtained was dried and evaporated to dryness. The oily residue obtained was dissolved in anhydrous ether and an ethereal solution of oxalic acid was added to give a precipitate of 0.97 g of 2-ethyl-3-(3,5-dimethyl-4-ω-di-n-butylaminopentoxy-benzoyl)-benzo[b]thiophene oxalate. Yield 22%; M.P. 73° C after recrystallization from benzene.

By the procedure described above and using the appropriate starting products, the following compound was prepared:

| Compound | Melting Point |
| --- | --- |
| 2-ethyl-3-(3,5-dimethyl-4-ω-di-n-propylamino-pentoxy-benzoyl)-benzo[b]thiophene oxalate | 108° C (benzene) |

EXAMPLE 4

2-Ethyl-3-(3,5-dimethyl-4-ω-di-n-propylaminohexyloxy-benzoyl)-benzo[b]thiophene oxalate.

a. Preparation of 2-ethyl-3-(3,5-dimethyl-4-ω-bromohexyloxy-benzoyl)-benzo[b]thiophene Into a 250 ml flask equipped with a mechanical stirrer and a dropping-funnel were introduced 9.33 g (0.03 mol) of 2-ethyl-3-(3,5-dimethyl-4-hydroxy-benzoyl)-benzo[b]thiophene and 10 g (0.06 mol) of anhydrous potassium carbonate with 100 ml of dimethylformamide.

While stirring, 23 ml (0.15 mol) of 1,6-dibromo-hexane were added and stirring was continued for 20 hours at room temperature. A mixture of water and ether was then added, the resulting organic phase was dried over anhydrous sodium sulphate and then carefully evaporated in order to eliminate the excess of 1,6-dibromohexane. The oily residue obtained was purified by dry column chromatography using silica as absorbent.

b. Preparation of 2-ethyl-3-(3,5-dimethyl-4-ω-di-n-propylaminohexyloxy-benzoyl)-benzo[b]thiophene oxalate Into a 100 ml flask equipped with a condenser and a dropping-funnel was introduced a solution of 3.9 g (0.0082 mol) of 2-ethyl-3-(3,5-dimethyl-4-ω-bromohexyloxy-benzoyl)-benzo[b]thiophene in 40 ml of benzene. To this solution were added 6.1 ml (0.041 mol) of di-n-propylamine and the mixture was refluxed for 24 hours. The reaction medium was then washed with water and the organic phase was dried and evaporated to dryness. The oily residue was dissolved in anhydrous ether and an ethereal solution of oxalic acid was added to give a precipitate of 2 g of 2-ethyl-3-(3,5-dimethyl-4-ω-di-n-propylaminohexyloxy-benzoyl)-benzo[b]thiophene oxalate. Yield 54%; M.P. 65° C.

By the procedure described above and using the appropriate starting products, the following compound was prepared:

| Compound | Melting Point |
| --- | --- |
| 2-ethyl-3-(3,5-dimethyl-4-ω-di-n-butylamino-hexyloxy-benzoyl)-benzo[b]thiophene oxalate | 92° C (benzene) |

EXAMPLE 5

2-Ethyl-3-(3,5-dimethyl-4-γ-di-n-butylaminopropoxy-benzoyl)-benzo[b]thiophene oxalate.

a. Preparation of 2-ethyl-3-acetyl-benzo[b]thiophene

Into a one-litre flask fitted with a mechanical stirrer and a dropping-funnel, 32.45 g (0.2 mol) of 2-ethyl-benzo[b]thiophene and 14.3 ml of acetyl chloride were introduced with 400 ml of dichloroethane. After the solution was cooled to between 5 and 10° C by means of an ice-bath, 23.2 ml (0.2 mol) of stannic chloride were introduced through the dropping-funnel. The mixture was then allowed to return to room temperature and was stirred for about 14 hours. The complex so formed was then hydrolysed with diluted hydrochloric acid. The organic and aqueous phases were separated by decantation and the aqueous phase was extracted with ether. The ethereal fraction was then added to the organic phase and the mixture was washed with water and evaporated to dryness to give, after distillation between 124°–134° C (0.01 mm/Hg), 31.3 g of 2-ethyl-3-acetyl-benzo[b]thiophene. Yield 76.5%.

Following the procedure described above and using the appropriate starting products the following compounds were prepared:

| Compound | Melting Point |
| --- | --- |
| 2-methyl-3-acetyl-benzo[b]thiophene | 68° C (after recrystallization from 100/140° C petroleum ether). |
| 2-n-propyl-3-acetyl-benzo[b]thiophene | 60° C (60/80° C petroleum ether) |
| 2-isopropyl-3-acetyl-benzo[b]thiophene | oily, not crystallized |
| 2-n-butyl-3-acetyl-benzo[b]thiophene | 59° C (100/140° C petroleum ether) |
| 2-cyclohexyl-3-acetyl-benzo[b]thiophene | b.p. 130–140° C (0.04 mm/Hg) | b. Preparation of 2-ethyl-3-carboxy-benzo[b]thiophene

Into a one-litre flask equipped with a mechanical stirrer and a dropping-funnel were introduced 39 g (0.97 mol) of sodium hydroxide with 270 ml of water. The solution was cooled to 0° C by means of an ice-bath and 20 ml (0.333 mol) of bromine were then added through the dropping-funnel followed by 190 ml of dioxan, care being taken to maintain the temperature at 0° C. Finally, still at the same temperature, a solution of 22.6 g (0.111 mol) of 2-ethyl-3-acetyl-benzo[b]thiophene in 25 ml of dioxan were introduced drop-by-drop. The mixture was then allowed to return to room temperature and stirring was maintained for 2 hours. A solution of sodium bisulphite was then added and the reaction medium was acidified and extracted with ether. The organic phase was washed with water, dried and evaporated to dryness to give 20.2 g of 2-ethyl-3-carboxy-benzo[b]thiophene. Yield 92%; M.P. 136° C.

By the procedure described above, the following compounds were prepared from the appropriate starting products:

| Compound | Melting Point |
| --- | --- |
| 2-methyl-3-carboxy-benzo[b]thiophene | 196° C (after recrystallization from benzene) |
| 2-n-propyl-3-carboxy-benzo[b]thiophene | 138° C (100/140° C petroleum ether) |
| 2-isopropyl-3-carboxy-benzo[b]thiophene | 175° C (acetic acid/water) |
| 2-n-butyl-3-carboxy-benzo[b]thiophene | 105° C (100/140° C petroleum ether) |
| 2-cyclohexyl-3-carboxy-benzo[b]thiophene | 213° C (ethanol) | c. Preparation of 2-ethyl-3-chlorocarbonyl-benzo[b]thiophene

Into a quarter-litre flask equipped with a condenser were introduced 27.2 g (0.128 mol) of 2-ethyl-3-carboxy-benzo[b]thiophene and 100 ml of thionyl chloride. The solution was refluxed for 3 hours and the excess of thionyl chloride was then eliminated by distillation. The residue was distilled and 27.1 g of 2-ethyl-3-chlorocarbonyl-benzo[b]thiophene were obtained representing a yield of 91%; b.p. 110/120° C (0.05 mm/Hg).

By the procedure described above, the following compounds were prepared from the appropriate starting products:

| Compound | Melting Point |
| --- | --- |
| 2-methyl-3-chlorocarbonyl-benzo[b]thiophene | 73° C (recrystallized from 100/140° C petroleum ether) |
| 2-n-propyl-3-chlorocarbonyl-benzo[b]thiophene | 33° C |
| 2-n-butyl-3-chlorocarbonyl-benzo[b]thiophene | 28° C |
| 2-cyclohexyl-3-chlorocarbonyl-benzo[b] | b.p. 170° C |

| Compound | Melting Point |
|---|---|
| thiophene | (0.03 mm/Hg) | d. Preparation of 2-ethyl-3-(3,5-dimethyl-4-methoxy-benzoyl)-benzo[b]thiophene

Into a half-litre flask equipped with a mechanical stirrer were introduced 27.1 g (0.121 mol) of 2-ethyl-3-chlorocarbonyl-benzo[b]thiophene, 16.5 g (0.121 mol) of 2,6-dimethyl-anisole and 120 ml of dichlorethane. The mixture was cooled to 5° C by means of an ice-bath and while stirring 24.2 g (0.181 mol) of aluminium chloride were added gradually.

The mixture was then allowed to return to room temperature and stirring was maintained for 24 hours.

The solution was hydrolysed with diluted hydrochloric acid and the organic and aqueous phases were separated by decantation. The organic phase was washed with water, then with a sodium hydroxide solution, and finally dried and evaporated to dryness.

The excess of 2,6-dimethyl-anisole was eliminated by heating under slight vacuum. 27.8 g of 2-ethyl-3-(3,5-dimethyl-4-methoxy-benzoyl)-benzo[b]thiophene were obtained. Yield 71%. Oily, not crystallized.

Following the procedure described above and using the appropriate starting products the following compounds were prepared:

| Compound | Melting Point |
|---|---|
| 2-methyl-3-(3,5-dimethyl-4-methoxy-benzoyl)-benzo[b]thiophene | 87° C (recrystallized from 40/80° C petroleum ether) |
| 2-n-propyl-3-(3,5-dimethyl-4-methoxy-benzoyl)-benzo[b]thiophene | Oily, not crystallized |
| 2-n-butyl-3-(3,5-dimethyl-4-methoxy-benzoyl)-benzo[b]thiophene | Oily, not crystallized |
| 2-cyclohexyl-3-(3,5-dimethyl-4-methoxy-benzoyl)-benzo[b]thiophene | Oily, not crystallized |
| 2-isopropyl-3-(3,5-dimethyl-4-methoxy-benzoyl)-benzo[b]thiophene | Oily, not crystallized | e. Preparation of 2-ethyl-3-(3,5-dimethyl-4-hydroxy-benzoyl)-benzo[b]thiophene

Into a half-litre flask equipped with a condenser, a mechanical stirrer and a thermometer, 25 g (0.777 mol) of 2-ethyl-3-(3,5-dimethyl-4-methoxy-benzoyl)-benzo[b]thiophene were introduced with 125 g of pyridine hydrochloride.

The solution was heated to 210° C for one hour and then poured on to slightly acidified ice. The organic fraction was extracted with ether and the ethereal solution obtained was washed with water, dried over anhydrous sodium sulphate and then evaporated to dryness to give, after two recrystallizations from 100/120° C petroleum ether, 12.1 g of 2-ethyl-3-(3,5-dimethyl-4-hydroxy-benzoyl)-benzo[b]thiophene. Yield 50%; M.P. 129° C.

By the procedure described above, the following compounds were prepared from the appropriate starting products:

| Compound | Melting Point |
|---|---|
| 2-methyl-3-(3,5-dimethyl-4-hydroxy-benzoyl)-benzo[b]thiophene | 167–168° C (after recrystallization from acetone 100–120° C petroleum ether). |
| 2-n-propyl-3-(3,5-dimethyl-4-hydroxy-benzoyl)-benzo[b]thiophene | 148° C (acetone/100–120° C petroleum ether) |
| 2-n-butyl-3-(3,5-dimethyl-4-hydroxy-benzoyl)-benzo[b]thiophene | 147° C (100/140° C petroleum ether) |
| 2-cyclohexyl-3-(3,5-dimethyl-4-hydroxy-benzoyl)-benzo[b]thiophene | 219° C (benzene) |
| 2-isopropyl-3-(3,5-dimethyl-4-hydroxy-benzoyl)-benzo[b]thiophene | 198–199° C (recrystallized from benzene) | f. Preparation of 2-ethyl-3-(3,5-dimethyl-4-γ-di-n-butylaminopropoxybenzoyl)-benzo[b]thiophene oxalate Into a quarter-litre flask equipped with a condenser and a dropping-funnel were introduced 4.75 g (0.015 mol) of 2-ethyl-3-(3,5-dimethyl-4-hydroxy-benzoyl)-benzo[b]thiophene, 4.15 g (0.03 mol) of anhydrous potassium carbonate, 90 ml of 1,2-dichloroethane and 2 ml of water. The mixture was refluxed for one hour and 41.1 g (0.02 mol) of 3-di-n-butylamino-2-chloropropane were then added, refluxing being continued for a further 8 hours.

The mixture was washed with water, dried and evaporated to dryness. The residue obtained was taken up in ether and then precipitated by means of oxalic acid. After two recrystallizations from ethyl acetate, 5 g of 2-ethyl-3-(3,5-dimethyl-4-γ-di-n-butylaminopropoxybenzoyl)-benzo[b]thiophene oxalate were obtained. Yield 88%; M.P. 127° C.

By the procedure described above and using the appropriate starting products, the compounds listed hereunder were prepared:

| Compound | Melting Point |
|---|---|
| 2-methyl-3-(3,5-dimethyl-4-γ-diethyl-aminopropoxy-benzoyl)-benzo[b]thiophene hydrochloride | 208° C (after recrystallization from ethyl acetate) |
| 2-methyl-3-(3,5-dimethyl-4-γ-di-n-propylaminopropoxy-benzoyl)-benzo[b]-thiophene hydrochloride | 163° C (ethyl acetate) |
| 2-methyl-3-(3,5-dimethyl-4-γ-di-n-butylaminopropoxy-benzoyl)-benzo[b]thiophene hydrochloride | 128° C (ethyl acetate) |
| 2-ethyl-3-(3,5-dimethyl-4-γ-di-n-propylaminopropoxy-benzoyl)-benzo[b]thiophene hydrochloride | 100° C (ethyl acetate/80–100° C petroleum ether) |
| 2-n-propyl-3-(3,5-dimethyl-4-γ-di-n-propylaminopropoxy-benzoyl)-benzo[b]thiophene oxalate | 127° C (ethyl acetate) |
| 2-n-propyl-3-(3,5-dimethyl-4-γ-di-n-butylaminopropoxy-benzoyl)-benzo[b]thiophene oxalate | 119° C (ethyl acetate) |
| 2-n-butyl-3-(3,5-dimethyl-4-γ-diethylamino-propoxy-benzoyl)-benzo[b]thiophene hydrochloride | 72–75° C (ethyl acetate) |
| 2-n-butyl-3-(3,5-dimethyl-4-γ-di-n-propyl-aminopropoxy-benzoyl)-benzo[b]thiophene oxalate | 122° C (ethyl acetate) |
| 2-cyclohexyl-3-(3,5-dimethyl-4-γ-di-n-propylaminopropoxy-benzoyl)-benzo[b]thiophene hydrochloride | 98–100° C (ethyl acetate) |
| 2-cyclohexyl-3-(3,5-dimethyl-4-γ-di-n-butyl-aminopropoxy-benzoyl)-benzo[b]thiophene oxalate | 156° C (ethyl acetate) |
| 2-n-butyl-3-(3,5-dimethyl-4-γ-di-n-butyl-aminopropoxy-benzoyl)-benzo[b]thiophene oxalate | 78° C (ethyl acetate) |

EXAMPLE 6

2-n-Propyl-3-(3,5-dimethyl-4-γ-dimethylamino-propoxy-benzoyl)-benzo[b]thiophene hydrochloride.

Into a 250 ml flask equipped with a condenser, 3.7 g (0.011 mol) of 2-n-propyl-3-(3,5-dimethyl-4-hydroxy-benzoyl)-benzo[b]thiophene were introduced with 5.1 g (0.037 mol) of anhydrous potassium carbonate, 3.5 g (0.011 mol) of 3-dimethylamino-1-tosyloxy-propane and 120 ml of benzene. The mixture was refluxed for two days and then washed with water. The organic phase was dried over anhydrous sodium sulphate and evaporated to dryness. The residue was dissolved in anhydrous ether and was reacted with an ethereal solution of hydrochloric acid to give 1.1 g of 2-n-propyl-3-(3,5-dimethyl-4-γ-dimethylaminopropoxy-benzoyl)-benzo[b]thiophene hydrochloride. Yield 24.5%; M.P. 134° C after recrystallization from ethyl acetate.

EXAMPLE 7

Tablets were prepared by granulating and compressing the following ingredients in accordance with known pharmaceutical techniques:

| Ingredient | mg per tablet |
|---|---|
| 2-methyl-3-(3,5-dimethyl-4-γ-di-n-butylaminopropoxy-benzoyl)-benzo[b]thiophene hydrochloride | 100 |
| Corn starch | 80 |
| Polyvinylpyrrolidone | 6 |
| Talc | 4 |
| Sodium carboxymethyl starch | 8 |
| Magnesium stearate | 2 |
| | 200 |

EXAMPLE 8

Hard gelatin capsules containing the following ingredients were prepared in accordance with known pharmaceutical techniques:

| Ingredient | mg per capsule |
|---|---|
| 2-methyl-3-(3,5-dimethyl-4-γ-di-n-butylaminopropoxy-benzoyl)-benzo[b]thiophene hydrochloride | 100 |
| STA-RX starch* | 128 |
| Colloidal silica | 2 |
| | 230 |

*A unique free-flowing starch such as produced by STALEY, U.S.A., which complies with the provisions of Food Additive Regulations. Also known under the T.M. "PRIMOGEL".

We claim:
1. 2-Methyl-3-(3,5-dimethyl-4-γ-di-n-butylaminopropoxy-benzoyl)-benzo[b]thiophene.

* * * * *